(12) United States Patent
McEwen et al.

(10) Patent No.: US 12,265,071 B2
(45) Date of Patent: Apr. 1, 2025

(54) SYSTEM AND METHOD FOR GAS REUSE IN TESTING OF HAZARDOUS GAS DETECTING INSTRUMENTS

(71) Applicant: HONEYWELL INTERNATIONAL INC., Charlotte, NC (US)

(72) Inventors: Shane Lee McEwen, Morris Plains, NJ (US); Jacob Thomas Spector, Morris Plains, NJ (US); Andrew Nilsson, Morris Plains, NJ (US); Chris Press, Morris Plains, NJ (US)

(73) Assignee: Honeywell International Inc., Charlotte, NC (US)

( * ) Notice: Subject to any disclaimer, the term of this patent is extended or adjusted under 35 U.S.C. 154(b) by 0 days.

(21) Appl. No.: 18/392,999

(22) Filed: Dec. 21, 2023

(65) Prior Publication Data

US 2024/0125751 A1 Apr. 18, 2024

Related U.S. Application Data

(63) Continuation of application No. 16/961,045, filed as application No. PCT/US2018/016656 on Feb. 2, 2018, now Pat. No. 11,933,773.

(51) Int. Cl.
*G01N 33/00* (2006.01)

(52) U.S. Cl.
CPC ....... *G01N 33/007* (2013.01); *G01N 33/0067* (2013.01); *G01N 33/0072* (2024.05)

(58) Field of Classification Search
CPC ......... G01N 33/007; G01N 2033/0072; G01N 2035/0403; G01N 2035/0405;
(Continued)

(56) References Cited

U.S. PATENT DOCUMENTS

| 6,119,507 A | 9/2000 | Flosbach et al. |
| 9,255,916 B2 | 2/2016 | Rambo et al. |
| (Continued) | | |

FOREIGN PATENT DOCUMENTS

| CN | 105353092 A | 2/2016 |
| IN | 367/MUM/2012 | 3/2012 |
| (Continued) | | |

OTHER PUBLICATIONS

U.S. Appl. No. 16/961,045, filed Jul. 9, 2020, 2020/0355659, Allowed.
(Continued)

*Primary Examiner* — John Fitzgerald
*Assistant Examiner* — Truong D Phan
(74) *Attorney, Agent, or Firm* — Alston & Bird LLP

(57) ABSTRACT

Embodiments relate generally to a gas detector test fixture that recycles test gas. A portable gas detector test fixture, comprises a test chamber, a processor, a docking connector communicatively coupled to the processor, an output device communicatively coupled to the processor, a memory communicatively coupled to the processor, and an application stored in the memory that, when executed by the processor, is configured to conduct a bump test on a portable gas detector plugged into the docking connector and to output the bump test result to the output device. The test fixture further comprises an inflow line configured to connect to a test gas supply line of a test gas container, where the inflow line is coupled to the test chamber, and an outflow line configured to connect to a test gas return line of the test gas container, where the outflow line is coupled to the test chamber.

16 Claims, 4 Drawing Sheets

(58) Field of Classification Search
CPC .......... G01N 33/0006; G01N 27/4163; G01N 27/4175; G01N 33/0067
See application file for complete search history.

(56) References Cited

U.S. PATENT DOCUMENTS

| | | | |
|---|---|---|---|
| 2010/0252455 | A1 | 10/2010 | Pratt et al. |
| 2010/0313962 | A1 | 12/2010 | Bondar et al. |
| 2014/0041436 | A1 | 2/2014 | Knott et al. |
| 2014/0342459 | A1* | 11/2014 | Berndt ................. G01N 33/007 422/83 |
| 2018/0148180 | A1* | 5/2018 | Fagundes ............... B64D 13/00 |

FOREIGN PATENT DOCUMENTS

| | | | |
|---|---|---|---|
| IN | 367/MUM2012 | A | 3/2012 |
| JP | 2006194776 | A * | 7/2006 |

OTHER PUBLICATIONS

CA Office Action Mailed on Jul 8, 2021for CA Application No. 3087363, 5 page(s).
Communication about decision to grant a European patent Mailed on Aug. 19, 2022for EP Application No. 18706054.
Communication about intention to grant a European patent Mailed on Apr. 7, 2022 for EP Application No. 18706054, 6 page(s).
Decision to grant a European patent Mailed on Aug. 19, 2022 for EP Application No. 18706054, 2 page(s).
Decision to grant a European patent Mailed on Nov. 30, 2023 for EP Application No. 22183226, 2 page(s).
EP Communication Pursuant to Rule 161(1) and 162 Mailed on Sep 9, 2020for EP Application No. 18706054.6, 3 page(s).
European search report Mailed on Oct. 18, 2022 for EP Application No. 22183226, 7 page(s).
European Search Report Mailed on Oct. 28, 2022for EP Application No. 22176165.
Examiner Interview Summary Record (PTOL-413) Mailed on Sep. 21, 2023 for U.S. Appl. No. 16/961,045, 1 page(s).
Intention to grant Mailed on Jul. 26, 2023 for EP Application No. 22183226, 9 page(s).
International Search Report and Written Opinion mailed on Nov. 27, 2018 for WO Application No. PCT/US18/016656.
Non-Final Rejection Mailed on Jun. 8, 2023 for U.S. Appl. No. 16/961,045, 13 page(s).
Notice of Allowance and Fees Due (PTOL-85) Mailed on Feb. 4, 2022 for CA Application No. 3087363.
Notice of Allowance and Fees Due (PTOL-85) Mailed on Oct. 19, 2023 for U.S. Appl. No. 16/961,045, 6 page(s).
Notice of Allowance and Fees Due (PTOL-85) Mailed on Sep. 21, 2023 for U.S. Appl. No. 16/961,045, 9 page(s).

* cited by examiner

SYSTEM AND METHOD FOR GAS REUSE IN TESTING OF HAZARDOUS GAS DETECTING INSTRUMENTS

CROSS-REFERENCE TO RELATED APPLICATIONS

This application is a continuation of a U.S. non-provisional patent application Ser. No. 16/961,045, entitled "System And Method For Gas Reuse In Testing Of Hazardous Gas Detecting Instruments" and filed on Jul. 9, 2020, which is herein incorporated by reference in its entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Portable gas detectors may be periodically tested to verify gas detection function. For example, a qualitative test, referred to as a "bump test," may be performed by flowing test gas over the gas detection sensors of the portable gas detector in a concentration and for a time duration suited to activate the alarm functions. If the portable gas detector alerts the presence of gas, the detector is deemed qualitatively functional; if the portable gas detector fails to alert the presence of gas, the detector is deemed qualitatively non-functional. Non-functional portable gas detectors may then be discarded, refurbished, maintained, or calibrated using different test and/or maintenance procedures. Additionally, by performing bump tests, workers may avoid carrying non-functional portable gas detectors in potentially hazardous work environments.

SUMMARY

In an embodiment, a portable gas detector test fixture is disclosed. The portable gas detector test fixture comprises a test chamber, a processor, a docking connector communicatively coupled to the processor, an output device communicatively coupled to the processor, a memory communicatively coupled to the processor, and an application stored in the memory that, when executed by the processor, is configured to conduct a bump test on a portable gas detector plugged into the docking connector and to output the bump test result to the output device. The portable gas detector test fixture further comprises an inflow line configured to connect to a test gas supply line of a test gas container, where the inflow line is coupled to the test chamber and an outflow line configured to connect to a test gas return line of the test gas container, where the outflow line is coupled to the test chamber.

In an embodiment, a method of bump testing a portable gas detector is disclosed The method comprises receiving a portable gas detector device into a test chamber of a gas detector test fixture and receiving the portable gas detector device into a docking connector of the gas detector test fixture, receiving test gas by the gas detector test fixture from a test gas container, flowing the received test gas over the portable gas detector device, determining a response of the portable gas detector device to the test gas by the gas detector test fixture, indicating the result of the bump test by the gas detector test fixture, and returning the received test gas to the test gas container, whereby the test gas is recycled.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
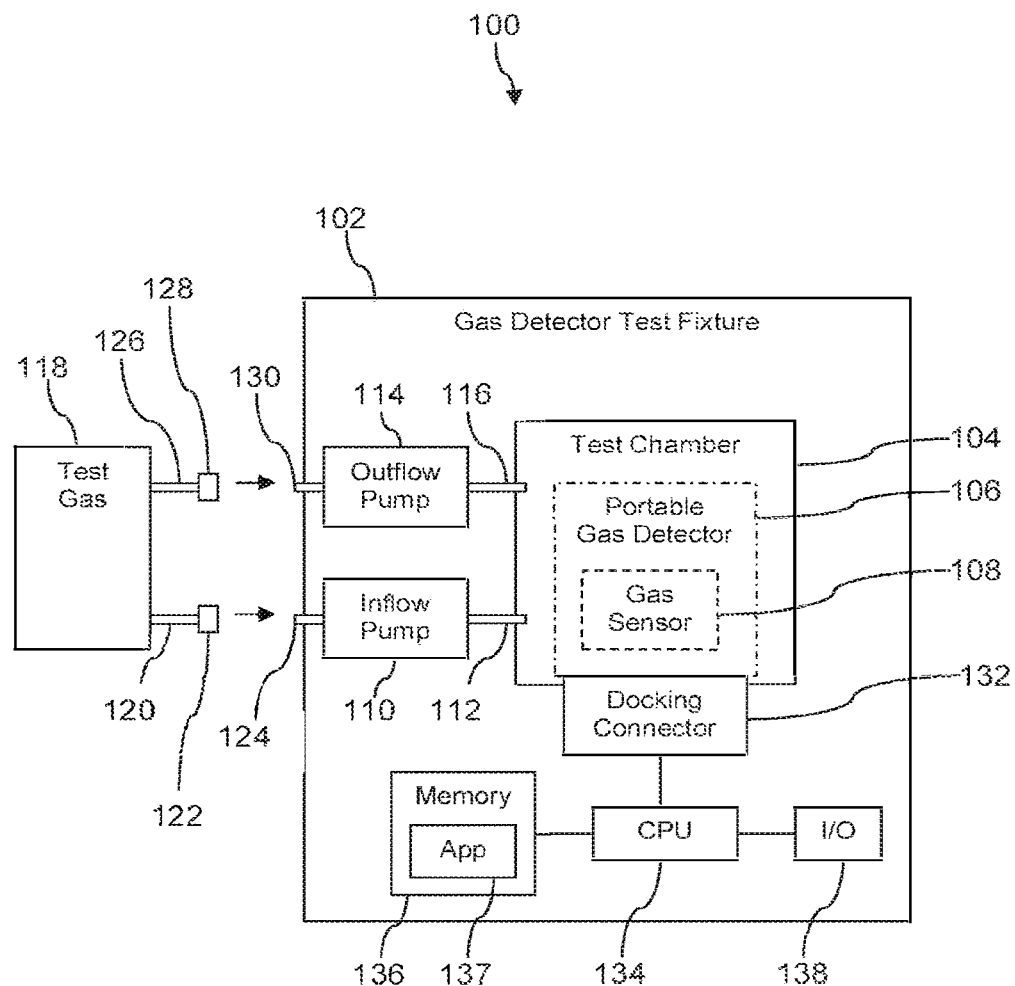
FIG. 1 is a block diagram of a portable gas detector test fixture and test environment according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments of the disclosure include methods and systems for recycling test gas in a portable gas detector test fixture. Test gas comprises a substantial part of the cost of performing periodic testing of portable gas sensors and/or portable gas detectors. For example, the global gas detection market may be about $800 M, and test gas usage may be about $400 M of that spend (about half annual costs may be in test gas). In some systems, the test gas is flowed into the test fixture from a test gas container, flowed over the portable gas detector, and then exhausted to the exterior of the test fixture. In an embodiment, vent hoods may further exhaust the test gas out of the test environment, for example out of a laboratory. These systems that exhaust the test gas waste a material resource (i.e., the test gas) that could be reused, thereby extending the utility of the resource and reducing the costs of operation. The present invention adapts the portable gas detector test fixture to recover and to reuse the test gas, thereby extending the life of the test gas. In some cases, a 10× reuse factor can be realized with legacy portable gas detector test fixtures. Said in another way, using the present invention may allow 10 times as many bump tests to be performed with a quantity of test gas than without the invention. This saves expense to businesses that utilize such portable gas detectors and periodically test those detectors. Further, this invention can reduce risks to human beings and the environment that may be posed by the previously exhausted test gas. In some embodiments, a test chamber of the potable gas detector test fixture may be altered to provide sealing along a door closure, whereby to increase further the recovery of test gas and reduce even further the exhausting of test gas to the exterior of the test fixture.

Embodiments of the disclosure relate to portable gas detector test fixtures that perform bump testing of portable gas detectors and/or multi-gas monitors and that recycle test gas.

Referring now to FIG. 1, a portable gas detector test fixture and testing environment 100 are described. In an embodiment, the test environment 100 comprises a portable gas detector test fixture 102, an external test gas container 118, and a portable gas detector 106 (i.e., the unit under test). The portable gas detector test fixture 102, which may be referred to as the test fixture 102 to promote concision, comprises a test chamber 104 into which a portable gas detector 106 may be received.

The portable gas detector 106 or multigas monitor comprises a gas sensor 108 that is sensitive to one or more gases of interest, for example hazardous gas. The portable gas detector 106 may be carried by a human being while in a potentially hazardous and/or potentially dangerous environment to alert them to the presence of dangerous gas. For example, the portable gas detector 106 may be carried by a fire fighter, by a refinery worker, by a chemical plant worker, by a hydrocarbon production facility worker, by a gas pipeline worker, or another worker. To assure that the portable gas detector 106 is functioning properly, it may be desirable to bump test the portable gas detector 106 periodically, for example monthly, weekly, daily, or on some other periodic interval. In some cases, if the portable gas detector 106 experiences an abnormal event, such as being dropped or being bumped into equipment, it may be desirable to test the portable gas detector 106 before a regularly scheduled retesting. For purposes of this patent application, the portable gas detector 106 may be considered to be a workpiece and not part of the portable gas detector test fixture 102.

The test fixture 102 may comprise an inflow pump 110, a test gas dispensing conduit 112, an outflow pump 114, and a test gas return conduit 116. Test gas pumped by the inflow pump 110 may flow out the test gas dispensing conduit 112 into the test chamber 104 to flow over the gas sensor 108 to excite the portable gas detector 106 to alert. The test gas may then be collected or recovered by the outflow pump 114 via the test gas return conduit 116 from the interior of the test chamber 104. In an embodiment, the text fixture 102 may comprise a single pump, either an inflow pump such as inflow pump 110 or an outflow pump such as outflow pump 114. In an embodiment, the inflow pump 110 and the outflow pump 114 may be integrated into a single component.

In an embodiment, an external test gas container 118 supplies test gas for performing bump testing of the portable gas detector 106 by the test fixture 102. The external test gas container 118 may comprise a source line 120, a source connector 122, a return line 126, and a return connector 128. The source connector 122 may connect the source line 120 to an inflow line 124 of the test fixture 102, where the inflow line 124 may supply test gas to the inflow pump 110 and/or to the test gas dispensing conduit 112. The return connector 128 may connect the return line 126 to an outflow line 130 of the test fixture 102, where the outflow line 130 may return test gas from the outflow pump 114 and/or from the test gas return conduit 116. When testing the portable gas detector 106, test gas may flow from the external test gas container 118 through the source line 120 to the inflow line 124, be pumped by the inflow pump 110 through the test gas dispensing conduit 112 and into the test chamber; this test gas may further flow from the test chamber 104 to the test gas return conduit 116, be pumped by the outflow pump 114 through the outflow line 130 to the return line 126 to return to the external test gas container 118.

In an embodiment, the test chamber 104 may not be well sealed, and some external air may be mixed with the test gas before returning to the external test gas container 118. In this way, over time the test gas may be diluted to such an extent as to be unserviceable for bump testing. In an embodiment, the external test gas container 118 may periodically be replaced with a fresh external test gas container 118 holding undiluted test gas. In an embodiment, the test fixture 102 may incorporate a test gas concentration and/or purity analysis functionality. In this case, the test fixture 102 may announce to a user when the external test gas container 118 is needed to be replaced and/or provide an advance announcement of impending need to replace the external test gas container 118. In some embodiments, the test chamber 104 may be provided with air-tight seals that prevent or reduce the rate of the degradation of test gas. The test gas may comprise one or more of Hydrogen Sulfide (H2S), volatile organic compounds (VOCs), combustible gas (e.g., methane (CH4) or other hydrocarbon), Carbon Monoxide (CO), high concentration oxygen (O2), Hydrogen Fluoride (HF), Hydrogen Cyanide (HCN), or other hazardous gases. The test gas may be a "quad gas" that comprises a mix of four different hazardous gases, such as combustible gas, H2S, CO, and high concentration O2.

The portable gas detector test fixture 102 may further comprise a docking connector 132, a processor 134, a memory 136, and an input/output device 138. When the portable gas detector 106 is received into the test chamber 104, an electrical port of the portable gas detector 106 connects to the docking connector 132. The docking connector 132 is communicatively coupled to the processor 134, thereby communicatively coupling the portable gas detector 106 to the processor 134. The processor 134 may execute a test application 137 or computer program stored in a non-transitory portion of the memory 136. The processor 134 may execute the test application 137 and/or provide execution parameters to the test application 137 based on user inputs provided using the input/output device 138 (e.g., switches, buttons, touchscreen). The processor 134, based on executing the test application 137, may control the pumps 110, 114 to turn them on and off. The processor 134, based on executing the test application 137, may open and close flow control valves (not shown) of the test fixture 102. The processor 134 may determine if the gas sensor 108 responds to the presence of test gas, if the portable gas detector 106 illuminates a visual alert, and if the portable gas detector 106 activates an audible alert. The alerts produced by the portable gas detector 106 may be provided via the docking connector 132 to the processor 134. Alternatively, the alerts produced by the portable gas detector 106 may be provided by an illuminating device (i.e., a light or LED) and a speaker device of the portable gas detector 106 which are received by a light sensor device and by a microphone device of the input/output 138. The processor 134 may output the results of the bump test to the input/output device 138 for display. The result may be indicated as pass or fail. If the indicated result is fail, further instructions or information may be presented on the input/output device 138, for example providing further details on what failure occurred of what alerting function failed or other.

In an embodiment, the processor 134 executing the test application 137 may determine an aging of the test gas stored in the external test gas container 118 and provide notifications to the user via the input/output device 138 indicating approximately when the external test gas container 118 should be replaced with a fresh container. In an embodiment, the test fixture 102 further comprises a test gas concentration sensor (not shown) that provides an input to the processor 134 that can be used in determining the aging of the test gas.

Figure 2:
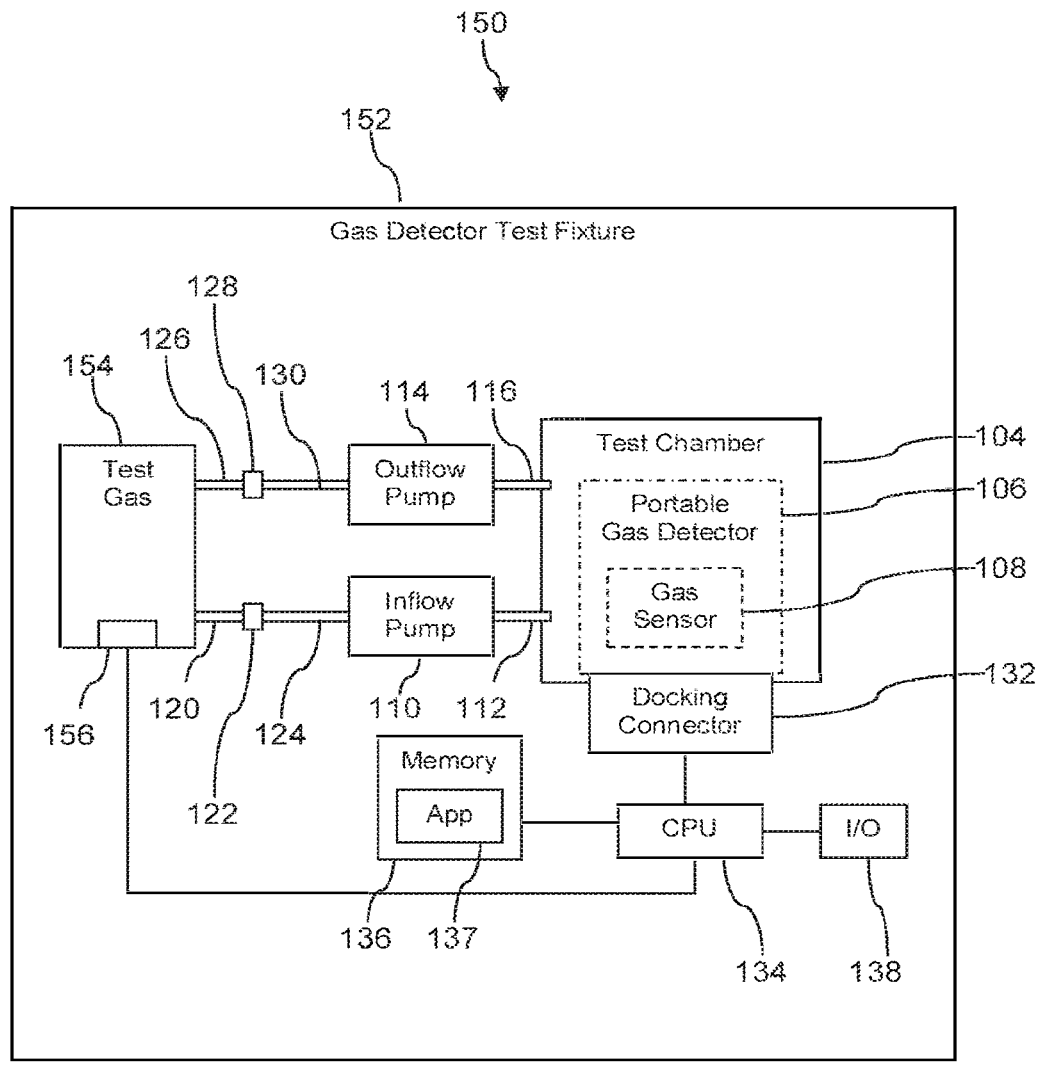
FIG. 2 is a block diagram of another portable gas detector test fixture and test environment according to an embodiment of the disclosure.

Turning now to FIG. 2, another test environment 150 and a different portable gas detector test fixture 152, which may be referred to as test fixture 152, is described. The test fixture 152 is substantially similar to the test fixture 102 illustrated in FIG. 1 and described above, with the provision that in the test fixture 152 of FIG. 2, the test gas is contained in an internal test gas container 154 that is located within a housing of the test fixture 152. In test fixture 152, the internal test gas container 154 may comprise a test gas concentration sensor 156 that is communicatively coupled to the processor 134, and the processor 134 may monitor the concentration of the test gas contained in the internal test gas container 154 and advise a user of the test fixture 152 (e.g., present a notification or an alert via the input/output device 138) when the internal test gas container 154 should be replaced with a fresh container. In some contexts, the internal test gas container 154 may be referred to as a replaceable gas container.

Figure 3:
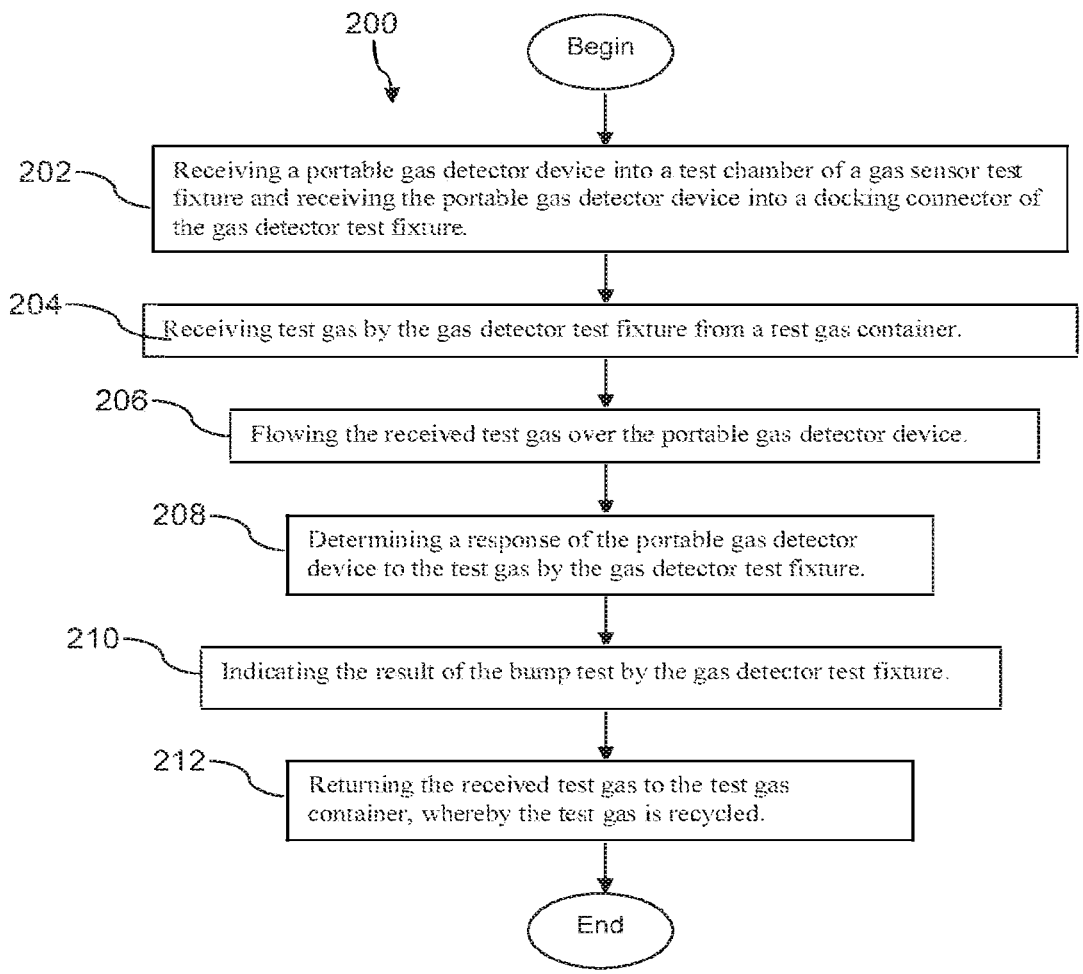
FIG. 3 is a flow chart of a method according to an embodiment of the disclosure.

Turning now to FIG. 3, a method 200 is described. The method 200 may be used to bump test a portable gas detector. At block 202, a portable gas detector device is received into a test chamber of a gas detector test fixture and into a docking connector of the gas detector test fixture. This may involve connecting the portable gas detector device into the docking connector of the gas detector test fixture, for example snapping it into place. This may include opening a hinged door of the gas detector test fixture to admit the portable gas detector device into the test chamber and closing the hinged door. At block 204, the gas detector test fixture receives inflow test gas from a test gas container. The test gas container may be external to the gas detector test fixture or it may be internal to the gas detector test fixture. The processing of this block may further include opening one or more valves to allow test gas to flow. At block 206, the received test gas is flowed over the portable gas detector device. At block 208, the gas detector test fixture determines a response of the portable gas detector device to the test gas. The response can be one or more alerts output by the portable gas detector device, for example, a flashing light, an illuminated light, an aural alert, vibration, or other alerting indication. At block 210, the gas detector test fixture indicates the result of the bump test. At block 212, the received test gas is returned to the test gas container, whereby the test gas is recycled. The method 200 may comprise additional processing blocks. For example, the method 200 may comprise sensing the concentration of the test gas in the test gas container, comparing the sensed concentration of test gas to a predefined threshold of test gas concentration, and presenting a message on an output device of the gas detector test fixture that the test gas will be unusable at a future indicated date or after an indicated number of future bump tests or presenting a message that the test gas is now unusable. The method 200 may further comprise attaching an external test gas container 118 to the gas detector test fixture by connecting the source line 120 of the external gas container 118 to the inflow line 124 of the gas detector test fixture 102 and connecting the return line 126 of the external gas container 118 to the outflow line 130 of the gas detector test fixture 102. The method 200 may further comprise installing an internal test gas container 154 into the gas detector test fixture 152, for example installing a replacement internal test gas container 154 by connecting the source line 120 of the internal gas container 154 to the inflow line 124 of the gas detector test fixture 152 and connecting the return line 126 of the internal gas container 154 to the outflow line 130 of the gas detector test fixture 152. The method 200 may further comprise turning on the portable gas detector that is being tested. The method 200 may further comprise turning off the portable gas detector after testing has been completed.

Figure 4:
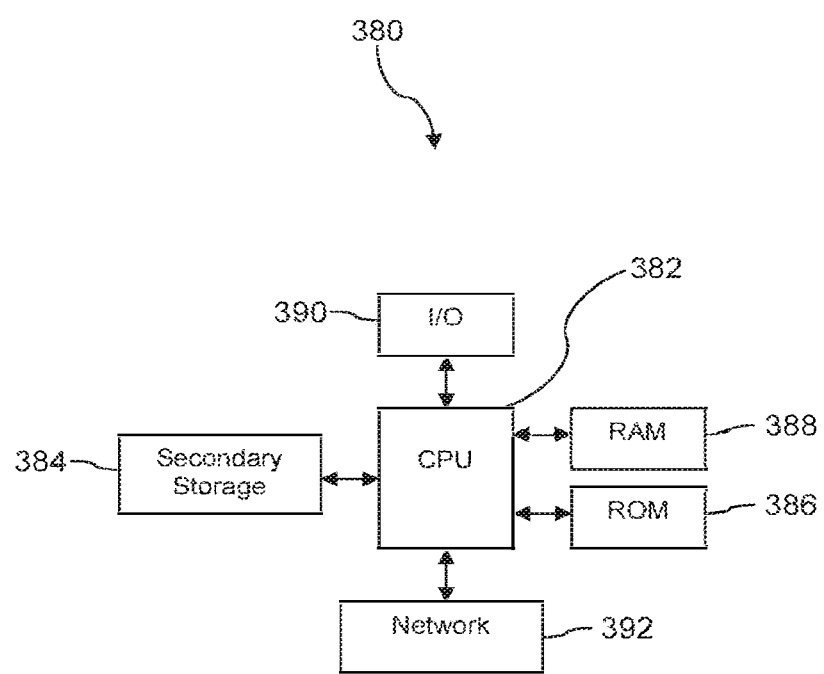
FIG. 4 is a block diagram of a computer system according to an embodiment of the disclosure.

FIG. 4 illustrates a computer system 380 suitable for implementing portions of one or more embodiments disclosed herein. For example, the processor 134, memory 136, and input/output device 138 can be considered to be a computer system. The computer system 380 may comprise a processor 382 (which may be referred to as a central processor unit or CPU) that is in communication with memory devices including secondary storage 384, read only memory (ROM) 386, random access memory (RAM) 388, input/output (I/O) devices 390, and network connectivity devices 392. The processor 382 may be implemented as one or more CPU chips. It is understood that the computer system 380 may not comprise all of the components listed. For example, the computer system 380 may not have secondary storage 384 or may not have network connectivity devices 392.

It is understood that by programming and/or loading executable instructions onto the computer system 380, at least one of the CPU 382, the RAM 388, and the ROM 386 are changed, transforming the computer system 380 in part into a particular machine or apparatus having the novel functionality taught by the present disclosure. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

Additionally, after the system 380 is turned on or booted, the CPU 382 may execute a computer program or application. For example, the CPU 382 may execute software or firmware stored in the ROM 386 or stored in the RAM 388. In some cases, on boot and/or when the application is initiated, the CPU 382 may copy the application or portions of the application from the secondary storage 384 to the RAM 388 or to memory space within the CPU 382 itself, and the CPU 382 may then execute instructions that the application is comprised of. In some cases, the CPU 382 may copy the application or portions of the application from memory accessed via the network connectivity devices 392 or via the I/O devices 390 to the RAM 388 or to memory space within the CPU 382, and the CPU 382 may then execute instructions that the application is comprised of. During execution, an application may load instructions into the CPU 382, for example load some of the instructions of the application into a cache of the CPU 382. In some contexts, an application that is executed may be said to configure the CPU 382 to do something, e.g., to configure the CPU 382 to perform the function or functions promoted by the subject application. When the CPU 382 is configured in this way by the application, the CPU 382 becomes a specific purpose computer or a specific purpose machine.

The secondary storage 384 is typically comprised of one or more disk drives or tape drives and is used for non-volatile storage of data and as an over-flow data storage device if RAM 388 is not large enough to hold all working data. Secondary storage 384 may be used to store programs which are loaded into RAM 388 when such programs are selected for execution. The ROM 386 is used to store instructions and perhaps data which are read during program execution. ROM 386 is a non-volatile memory device which typically has a small memory capacity relative to the larger memory capacity of secondary storage 384. The RAM 388 is used to store volatile data and perhaps to store instructions. Access to both ROM 386 and RAM 388 is typically faster than to secondary storage 384. The secondary storage 384, the RAM 388, and/or the ROM 386 may be referred to in some contexts as computer readable storage media and/or non-transitory computer readable media.

I/O devices 390 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 392 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards that promote radio communications using protocols such as code division multiple access (CDMA), global system for mobile communications (GSM), long-term evolution (LTE), world-wide interoperability for microwave access (WiMAX), near field communications (NFC), radio frequency identity (RFID), and/or other air interface protocol radio transceiver cards, and other well-known network devices. These network connectivity devices 392 may enable the processor 382 to communicate with the Internet or one or more intranets. With such a network connection, it is contemplated that the processor 382 might receive information from the network, or might output information to the network in the course of performing the above-described method steps. Such information, which is often represented as a sequence of instructions to be executed using processor 382, may be received from and outputted to the network, for example, in the form of a computer data signal embodied in a carrier wave.

Such information, which may include data or instructions to be executed using processor 382 for example, may be received from and outputted to the network, for example, in the form of a computer data baseband signal or signal embodied in a carrier wave. The baseband signal or signal embedded in the carrier wave, or other types of signals currently used or hereafter developed, may be generated according to several methods well-known to one skilled in the art. The baseband signal and/or signal embedded in the carrier wave may be referred to in some contexts as a transitory signal.

The processor 382 executes instructions, codes, computer programs, scripts which it accesses from a hard disk, floppy disk, optical disk (these various disk based systems may all be considered secondary storage 384), flash drive, ROM 386, RAM 388, or the network connectivity devices 392. While only one processor 382 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 384, for example, hard drives, floppy disks, optical disks, and/or other device, the ROM 386, and/or the RAM 388 may be referred to in some contexts as non-transitory instructions and/or non-transitory information.

In an embodiment, the computer system 380 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computer system 380 to provide the functionality of a number of servers that is not directly bound to the number of computers in the computer system 380. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an embodiment, some or all of the functionality disclosed above may be provided as a computer program product. The computer program product may comprise one or more computer readable storage medium having computer usable program code embodied therein to implement the functionality disclosed above. The computer program product may comprise data structures, executable instructions, and other computer usable program code. The computer program product may be embodied in removable computer storage media and/or non-removable computer storage media. The removable computer readable storage medium may comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 380, at least portions of the contents of the computer program product to the secondary storage 384, to the ROM 386, to the RAM 388, and/or to other non-volatile memory and volatile memory of the computer system 380. The processor 382 may process the executable instructions and/or data structures in part by directly accessing the computer program product, for example by reading from a CD-ROM disk inserted into a disk drive peripheral of the computer system 380. Alternatively, the processor 382 may process the executable instructions and/or data structures by remotely accessing the computer program product, for example by downloading the executable instructions and/or data structures from a remote server through the network connectivity devices 392. The computer program product may comprise instructions that promote the loading and/or copying of data, data structures, files, and/or executable instructions to the secondary storage 384, to the ROM 386, to the RAM 388, and/or to other non-volatile memory and volatile memory of the computer system 380.

In some contexts, the secondary storage 384, the ROM 386, and the RAM 388 may be referred to as a non-transitory computer readable medium or a computer readable storage media. A dynamic RAM embodiment of the RAM 388, likewise, may be referred to as a non-transitory computer readable medium in that while the dynamic RAM receives electrical power and is operated in accordance with its design, for example during a period of time during which the computer system 380 is turned on and operational, the dynamic RAM stores information that is written to it. Similarly, the processor 382 may comprise an internal RAM, an internal ROM, a cache memory, and/or other internal non-transitory storage blocks, sections, or components that may be referred to in some contexts as non-transitory computer readable media or computer readable storage media.

Having described various devices and methods herein, exemplary embodiments or aspects can include, but are not limited to:

In a first embodiment, a portable gas test fixture can comprise a test chamber, a processor, a docking connector communicatively coupled to the processor, an output device communicatively coupled to the processor, a memory communicatively coupled to the processor, an application stored in the memory that, when executed by the processor, is configured to conduct a bump test on a portable gas detector plugged into the docking connector and to output the bump test result to the output device, an inflow line configured to connect to a test gas supply line of a test gas container, where the inflow line is coupled to the test chamber, and an outflow line configured to connect to a test gas return line of the test gas container, where the outflow line is coupled to the test chamber.

A second embodiment can include the portable gas detector test fixture of the first embodiment, wherein the test gas container is internal to the portable gas detector test fixture.

A third embodiment can include the portable gas detector test fixture of the first embodiment, wherein the test gas container is external to the portable gas detector test fixture.

A fourth embodiment can include the portable gas detector test fixture of the first embodiment, wherein the test gas container stores Hydrogen Sulfide (H2S).

A fifth embodiment can include the portable gas detector test fixture of the first embodiment, wherein the test gas container stores Carbon Monoxide (CO).

A sixth embodiment can include the portable gas detector test fixture of the first embodiment, wherein the test gas container stores Hydrogen Fluoride (HF).

A seventh embodiment can include the portable gas detector test fixture of the first embodiment, wherein the test gas container stores Hydrogen Cyanide (HCN).

An eighth embodiment can include the portable gas detector test fixture of the first embodiment, wherein the test gas container stores volatile organic compounds (VOCs).

A ninth embodiment can include the portable gas detector test fixture of the first embodiment, wherein the test gas container stores combustible gas.

A tenth embodiment can include the portable gas detector test fixture of the first embodiment, wherein the test gas container stores high concentration oxygen (O2).

In an eleventh embodiment, a method of bump testing a portable gas detector may comprise receiving a portable gas detector device into a test chamber of a gas detector test fixture and receiving the portable gas detector device into a docking connector of the gas detector test fixture, receiving test gas by the gas detector test fixture from a test gas container, flowing the received test gas over the portable gas detector device, determining a response of the portable gas detector device to the test gas by the gas detector test fixture, indicating the result of the bump test by the gas detector test fixture, and returning the received test gas to the test gas container, whereby the test gas is recycled.

A twelfth embodiment can include the method of the eleventh embodiment, wherein the test gas container is an external gas container, and the method further comprising connecting a source line of the external gas container to an inflow line of the gas detector test fixture and connecting a return line of the external gas container to an outflow line of the gas detector test fixture.

A thirteenth embodiment can include the method of the eleventh embodiment, wherein the test gas container is an internal gas container, and the method further comprising connecting a source line of the internal gas container to an inflow line of the gas detector test fixture and connecting a return line of the internal gas container to an outflow line of the gas detector test fixture.

A fourteenth embodiment can include the method of the eleventh embodiment, further comprising sensing a concentration of test gas in the test gas container, comparing the sensed concentration of test gas to a predetermined threshold of test gas concentration, and presenting a message on an output device of the gas detector test fixture about the test gas.

A fifteenth embodiment can include the method of the eleventh embodiment, further comprising turning off the portable gas detector after testing has been completed.

A sixteenth embodiment can include the method of the fifteenth embodiment, further comprising turning off the portable gas detector after testing has been completed.

A seventeenth embodiment can include the method of the eleventh embodiment, wherein receiving the test gas comprises pumping the test gas by a pump of the gas detector test fixture.

An eighteenth embodiment can include the method of the eleventh embodiment, wherein returning the received test gas comprises pumping the test gas by the gas detector test fixture.

A nineteenth embodiment can include the method of the eleventh embodiment, wherein the test gas comprises one or more of Hydrogen Sulfide (H2S), Carbon Monoxide (CO), Hydrogen Fluoride (HF), Hydrogen Cyanide (HCN), or high concentration Oxygen (O2).

A twentieth embodiment can include the method of the eleventh embodiment, wherein the test gas comprises one or more of volatile organic compounds (VOCs) or combustible gas.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A portable gas detector test fixture, comprising:
   a test chamber;
   a processor;
   a test gas container storing a test gas;
   a docking connector communicatively coupled to the processor;
   an output device communicatively coupled to the processor;
   a memory communicatively coupled to the processor;
   an application stored in the memory that, when executed by the processor, is configured to determine an aging of the test gas stored in the test gas container and to provide a notification to a user via the output device indicating when the test gas container should be replaced based on the determined aging of the test gas, wherein the aging of the test gas is caused by a degradation of the test gas over time;
   an inflow pump configured to connect to a test gas source line of the test gas container, where the inflow pump is coupled to the test chamber; and
   an outflow pump configured to connect to a test gas return line of the test gas container, wherein the outflow pump is coupled to the test chamber, wherein the test gas is returned to the test gas container and reused.

2. The portable gas detector test fixture of claim 1, wherein the application, when executed by the processor, is configured to conduct a bump test on a portable gas detector plugged into the docking connector and to output a bump test result to the output device.

3. The portable gas detector test fixture of claim 1, wherein one end of the inflow pump is connected to an inflow line and another end of the inflow pump is connected to a test gas dispensing conduit.

4. The portable gas detector test fixture of claim 1, wherein one end of the outflow pump is connected to an outflow line and another end of the outflow pump is connected to a test gas return conduit.

5. The portable gas detector test fixture of claim 1, wherein the test gas container is internal to the portable gas detector test fixture.

6. The portable gas detector test fixture of claim 1, wherein the test gas container is external to the portable gas detector test fixture.

7. The portable gas detector test fixture of claim 1 further comprising a source connector connecting the test gas source line to an inflow line.

8. The portable gas detector test fixture of claim 1 further comprising a return connector connecting the test gas return line to an outflow line.

9. The portable gas detector test fixture of claim 1, wherein the test chamber is provided with an air-tight seal to reduce a rate of the degradation of the test gas.

10. The portable gas detector test fixture of claim 1, wherein the application, when executed by the processor, controls the inflow pump and the outflow pump to turn on and off.

11. The portable gas detector test fixture of claim 1, wherein the application, when executed by the processor, controls flow control valves of the portable gas detector test fixture to open and close.

12. The portable gas detector test fixture of claim 1, wherein the inflow pump is configured to pump received test gas, and wherein the outflow pump is configured to pump returning test gas.

13. The portable gas detector test fixture of claim 1, wherein the test gas container or the portable gas detector test fixture comprises a test gas concentration sensor communicatively coupled to the processor.

14. A method of determining an aging of a test gas stored in a test gas container of a portable gas detector test fixture, comprising:

executing a test application by a processor which causes the test application to sense a concentration of the test gas in the test gas container;

comparing the sensed concentration of the test gas to a predefined threshold of test gas concentration to determine the aging of the test gas; and presenting a message on an output device of the portable gas detector test fixture, wherein the message indicates when the test gas container is to be replaced based on the determined aging of the test gas, wherein the aging of the test gas is caused by degradation of the test gas over time due to reuse of the test gas stored in the test gas container.

15. The method of claim 14, wherein the test gas comprises one or more of Hydrogen Sulfide ($H_2S$), Carbon Monoxide (CO), Hydrogen Fluoride (HF), Hydrogen Cyanide (HCN), high concentration Oxygen ($O_2$), volatile organic compounds (VOCs), or combustible gas.

16. The method of claim 14, wherein the message indicates at least a future date or a number of bump tests after which the test gas stored in the test gas container becomes unusable.

* * * * *